(12) United States Patent
Cortial et al.

(10) Patent No.: US 8,507,397 B2
(45) Date of Patent: Aug. 13, 2013

(54) ORGANOMETALLIC COMPOUNDS CONTAINING A METAL BELONGING TO THE SECOND COLUMN OF THE PERIODIC TABLE, AND METHOD FOR PREPARING SAME

(75) Inventors: Guillaume Cortial, Clermont-Ferrand (FR); Pascal Le Floch, Orsay (FR); Françoise Hervagault, legal representative, Orsay (FR); Elaine Le Floch, legal representative, Orsay (FR); Clémence Le Floch, legal representative, Orsay (FR); Paul Le Floch, legal representative, Orsay (FR); Francois Nief, Antony (FR); Julien Thuilliez, La Roche-Blanche (FR)

(73) Assignees: Campagnie Generale des Etablissements Michelin, Clermont-Ferrand (FR); Michelin Recherche et Technique S.A., Granges-Paccot (CH); Centre National de la Recherche Scientific, Paris Cedex (FR); Ecole Polytechnique, Palaiseau Cedex (FR)

( * ) Notice: Subject to any disclaimer, the term of this patent is extended or adjusted under 35 U.S.C. 154(b) by 0 days.

(21) Appl. No.: 13/375,725

(22) PCT Filed: Jun. 1, 2010

(86) PCT No.: PCT/EP2010/003307
§ 371 (c)(1),
(2), (4) Date: Feb. 17, 2012

(87) PCT Pub. No.: WO2010/139450
PCT Pub. Date: Dec. 9, 2010

(65) Prior Publication Data
US 2012/0135857 A1 May 31, 2012

(30) Foreign Application Priority Data
Jun. 2, 2009 (FR) .................. 09 02652

(51) Int. Cl.
C08F 4/50 (2006.01)
C07F 3/02 (2006.01)
(52) U.S. Cl.
USPC .......................... 502/154; 564/305
(58) Field of Classification Search
None
See application file for complete search history.

(56) References Cited

U.S. PATENT DOCUMENTS

| 4,550,142 | A | 10/1985 | Akita et al. |
|---|---|---|---|
| 5,066,721 | A | 11/1991 | Hamada et al. |
| 5,665,812 | A | 9/1997 | Gorce et al. |
| 6,013,718 | A | 1/2000 | Cabioch et al. |
| 6,838,534 | B2 | 1/2005 | Laubry |
| 2004/0009870 | A1 | 1/2004 | Laubry |
| 2005/0130835 | A1 | 6/2005 | Laubry et al. |

FOREIGN PATENT DOCUMENTS

| EP | 0 692 492 A1 | 1/1996 |
|---|---|---|
| EP | 0 692 493 A1 | 1/1996 |
| EP | 0 778 311 A1 | 6/1997 |
| EP | 1 355 960 A1 | 10/2003 |
| EP | 1 509 557 A1 | 3/2005 |
| WO | WO 02/38636 A1 | 5/2002 |
| WO | WO 03/097708 A1 | 11/2003 |

OTHER PUBLICATIONS

International Search Report (PCT/ISA/210) issued on Jun. 16, 2010, by European Patent Office as the International Searching Authority for International Application No. PCTEP2010/003307.
Sjoerd Harder et al., "Dimeric Benzylcalcium Complexes: Influence of THF in Stereoselective Styrene Polymerization", Organometallics, 2002, vol. 21, No. 11, pp. 2268-2274, XP-002561496.

*Primary Examiner* — Melvin Curtis Mayes
*Assistant Examiner* — Yun Qian
(74) *Attorney, Agent, or Firm* — Buchanan Ingersoll & Rooney PC

(57) ABSTRACT

The present invention relates to a novel organometallic compound based on a divalent metal belonging to the $2^{nd}$ column of the Periodic Table that can be used as an alkylating agent in a catalytic system based on a rare-earth metal. This novel compound corresponds to the formula:

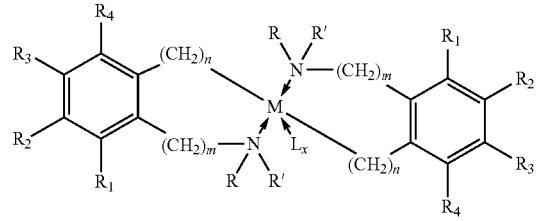

Formula I in which,
M is a metal belonging to the $2^{nd}$ column of the Periodic Table, chosen from Be, Mg, Sr, Ba, and Ra; $R_1$, $R_2$, $R_3$ and $R_4$ are hydrogen atoms or alkyl or aryl substituents, optionally bonded together to form at least one ring or at least one aromatic ring; R and R' denote alkyl or aryl substituents; L is a Lewis base; x is an integer from 0 to 4; m is an integer greater than or equal to 0; and n is an integer greater than or equal to 1.

2 Claims, No Drawings

ORGANOMETALLIC COMPOUNDS CONTAINING A METAL BELONGING TO THE SECOND COLUMN OF THE PERIODIC TABLE, AND METHOD FOR PREPARING SAME

The present invention relates to a novel organometallic compound based on a divalent metal belonging to the $2^{nd}$ column of the Periodic Table that can be used as an alkylating co-catalyst in a catalytic system for polymerization based on a rare earth. The present invention also relates to a process for preparing said novel organometallic compound.

Now that savings in fuel and the need to protect the environment have become a priority, it is desirable to produce mixtures having good mechanical properties and a hysteresis which is as low as possible in order to be able to employ them in the form of rubber compositions which can be used in the manufacture of various semi-finished products incorporated into the composition of tyres, such as, for example, underlayers, sidewalls or treads, and in order to obtain tyres having an increasingly reduced rolling resistance. In order to achieve such an objective, it has been proposed to modify the structure of the diene polymers and copolymers at the end of polymerization by means of functionalizing, coupling or star-branching agents in order to introduce into the elastomer an interactive function with respect to the filler (or fillers) used in the rubber composition.

A very large majority of these solutions firstly concentrated on the use of functionalized polymers that are active with respect to carbon black, for the purpose of obtaining a good interaction between the polymer thus modified and the carbon black.

More recently, modified elastomers that are active with respect to silica have been developed for the purpose of obtaining a good interaction between the polymer thus modified and the silica.

When the diene elastomers are obtained by polymerization of the monomers in the presence of a catalytic system based on a rare earth, as described in particular in patent documents EP 1 355 960 A1 or EP 1 509 557 B1 by the applicants, it is possible to envisage a functionalization with agents bearing a function suitable for the application envisaged for the functionalized diene elastomer.

As a functionalizing agent that can be used for this functionalizing step, it is possible to envisage those used in the prior art for functionalizing diene elastomers resulting from the anionic polymerization in the presence of a catalyst based on an organic compound of an alkali metal.

By way of illustration of this prior art relating to the interaction with carbon black, mention may be made, for example, of the chain-end modification of diene elastomers by agents such as 4,4'-bis(diethylamino)benzophenone as described in U.S. Pat. No. 4,550,142 or halogenated derivatives of tin, or else the grafting along the polymer chain of functions active with respect to carbon black.

By way of illustration of this prior art relating to the interaction with silica, mention may be made, for example, of the U.S. Pat. No. 5,066,721, which describes a rubber composition comprising a diene polymer functionalized by an alkoxysilane having at least one unhydrolysed alkoxy residue. In patent documents EP 0 692 492 A1 and EP 0 692 493 A1, in the name of the applicants, the functionalization of diene elastomers by an alkoxysilane group, using a functional agent such as an epoxidized alcoxysilane, is described. Document EP 0 778 311 A1 discloses diene polymers bearing, at the chain end, a silanol function or a polysiloxane block having a silanol end that are obtained by reaction, at the end of polymerization, of cyclic polysiloxanes with the living polymers.

The method for synthesizing functionalized polymers using a catalytic system based on a rare earth has the advantage of resulting in diene elastomers possessing chemical functions at the chain end of varied structure, depending on the choice of the functional agent used.

However, one drawback is that the synthesis comprises several steps, which may result in a higher cost during the manufacture of such a polymer on the industrial scale, for example linked to the use of a larger number of reactors and therefore to a complicated implementation.

Another drawback is the control of the purity of the functionalizing agent, which depending on the case, may result in deactivation or termination reactions of the ends of the growing polymer chains, the cause of a higher or lower proportion of unfunctionalized elastomer chains.

The present invention proposes to contribute to overcoming the drawbacks encountered in the prior art in the preparation of functionalized elastomers.

During their research, the inventors have discovered a novel organometallic compound based on a divalent metal belonging to the $2^{nd}$ column of the Periodic Table. This novel oranometallic compound combined with a rare-earth metal salt can form a catalytic system for polymerization which makes it possible, in particular, to limit the number of steps for synthesizing a chain-end functionalized diene elastomer, while ensuring an optimal functionalization, i.e. close or equal to 100%.

The use of this novel oranometallic compound in a catalytic system based on a rare-earth metal salt for polymerization and more particularly for preparing functionalized diene elastomers, makes it possible to do away with the subsequent step of reacting with a functionalizing agent. The functionalized diene elastomers thus obtained have a high level of functionalization, up to 100%, and may advantageously be used in rubber compositions comprising a reinforcing filler and intended for a tyre application.

A first subject of the present invention is therefore a novel organometallic compound based on a metal belonging to the $2^{nd}$ column of the Periodic Table.

Another subject of the invention is a process for preparing this novel compound.

Another subject of the invention is the use of this novel compound as a co-catalyst in a catalytic system based on a rare-earth metal salt.

Of course, the expression "based on" used to define the constituents of the catalytic system is understood to mean the mixture of these constituents and/or the product of the reaction between these constituents. Moreover, any range of values denoted by the expression "between a and b" represents the field of values ranging from more than a to less than b (that is to say limits a and b excluded) whereas any range of values denoted by the expression "from a to b" means the field of values ranging from a up to b (that is to say including the strict limits a and b).

Thus, a first subject of the present invention is an organometallic compound based on a metal belonging to the $2^{nd}$ column of the Periodic Table and corresponding to the formula (I):

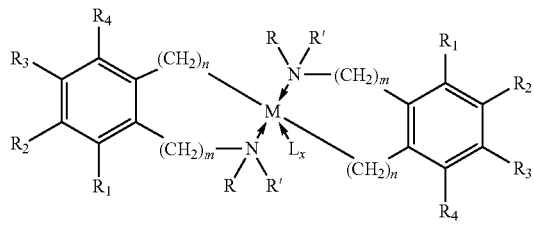

Formula I in which:
M is a metal belonging to the 2$^{nd}$ column of the Periodic Table, chosen from Be, Mg, Sr, Ba and Ra;
$R_1$, $R_2$, $R_3$, $R_4$, which are identical to or different from one another, are hydrogen atoms or linear or branched alkyl substituents, or aryl substituents, which are substituted or unsubstituted, optionally bonded together ($R_1$ is then bonded to $R_{i+1}$) to form at least one ring composed of 5 or 6 atoms, or at least one aromatic ring;
R and R' denote linear or branched alkyl substituents, or aromatic substituents, which are substituted or unsubstituted, which are identical to or different from one another;
L is a Lewis base;
x is an integer that is equal to 0, 1, 2, 3 or 4;
m is an integer greater than or equal to 0 and less than or equal to 3;
n is an integer greater than or equal to 1 and less than or equal to 3.
In this formula (I), M is preferably magnesium.
When $R_1$, $R_2$, $R_3$ or $R_4$ denotes an alkyl substituent, this is preferably a $C_1$-$C_{12}$, and more preferably still $C_1$-$C_6$, alkyl substituent.
When $R_1$, $R_2$, $R_3$ or $R_4$ denotes an aryl substituent, this is preferably a $C_6$-$C_{12}$, and more preferably still $C_6$-$C_{10}$, aryl substituent.
When $R_1$, $R_2$, $R_3$ or $R_4$ are bonded together to form a ring containing 5 or 6 carbon atoms, the unit obtained is preferably composed of 2 to 4 conjugated aromatic rings, and more preferably of 2 to 3 rings.
Preferably $R_1$, $R_2$, $R_3$ and $R_4$ are hydrogen atoms.
When R or R' denotes an alkyl substituent, this is preferably a $C_1$-$C_6$, and more preferably still $C_1$-$C_4$, alkyl substituent.
When R or R' denotes an aryl substituent, this is preferably a $C_6$-$C_{12}$, and more preferably still $C_5$-$C_6$, aryl substituent.
Preferably R and R' are methyl, ethyl, isopropyl, n-butyl, isobutyl or tert-butyl groups.
In the formula (I), n is an integer preferably equal to 1.
In the formula (I), m is an integer preferably equal to 0 or 1, m is more preferably equal to 1.
In the formula (I), L is a Lewis base. According to the invention, the Lewis base is particularly chosen from amines or ethers. Preferably, the Lewis base is pyridine or tetrahydrofuran (THF).
As the organometallic compound of formula (I), mention may be made, by way of example, of bis(ortho-N,N-dimethylaminobenzyl)magnesium, for which $R_1$, $R_2$, $R_3$ and $R_4$ are hydrogen atoms, R and R' are methyl groups, m is equal to 0, n is equal to 1, x is equal to 1 and L is THF.
Another subject of the invention is a method of synthesizing a compound of formula (I) described above.
A method of preparing these compounds of formula (I) according to the invention comprises the following steps:
(a) of synthesizing a salt based on an alkali metal and corresponding to the formula (II):

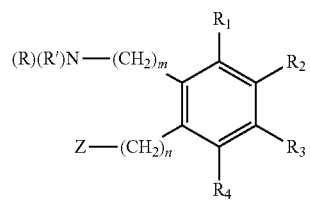

Formula II $R_1$, $R_2$, $R_3$, $R_4$, R, R', n and m are as defined above in the formula (I);
Z is a lithium, sodium or potassium atom;
(b) of reacting the compound of formula (II) obtained in the preceding step with a salt of a metal belonging to the 2$^{nd}$ column of the Periodic Table, chosen from Be, Mg, Sr, Ba, and Ra;
(c) of recovering the organometallic compound of formula (I) obtained.
Each of the steps takes place in a polar or apolar solvent or in a mixture of polar and apolar solvents.
By way of illustration, in step (a), the alkali metal salt may be synthesized starting from dimethylaminotoluene in the presence of an organolithium compound and optionally a potassium alcoholate.
In step (b), the salt of a metal belonging to the 2$^{nd}$ column of the Periodic Table is preferably a halide, more particularly a chloride. The metal belonging to the 2$^{nd}$ column of the Periodic Table is preferably magnesium. The salt of a metal belonging to the 2$^{nd}$ column of the Periodic Table is used in proportions such that the (compound of formula (II)/salt) molar ratio ranges from 1.5 to 2.5, preferably from 1.8 to 2.2, more preferably still substantially equal to 2.
In step (c), the recovery of the organometallic compound of formula (I) obtained in the preceding step is carried out in a manner known per se, for example by evaporation of the synthesis solvent or by recrystallization in a solvent or a mixture of solvents.
Similar methods are described in particular in the document by Bailey et al. in Chem. Eur. J. 2003, 9, 4820-4828.
Another subject of the invention is the use of an organometallic compound of formula (III):

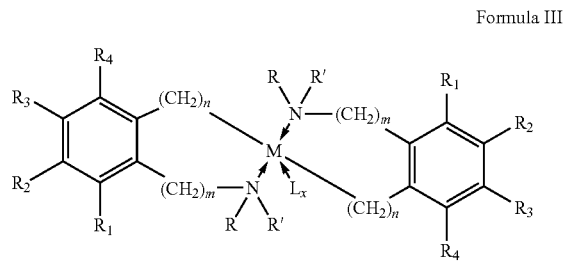

Formula III in which,
M is a metal belonging to the 2$^{nd}$ column of the Periodic Table, namely chosen from Be, Mg, Sr, Ba, Ra and Ca;
$R_1$, $R_2$, $R_3$, $R_4$, which are identical to or different from one another, are hydrogen atoms or linear or branched alkyl substituents, or aryl substituents, which are substituted or unsubstituted, optionally bonded together to form at least one ring composed of 5 or 6 atoms, or at least one aromatic ring;

R and R', which are identical to or different from one another, denote linear or branched alkyl substituents, or aryl substituents, which are substituted or unsubstituted;

L is a Lewis base;

x is an integer which is equal to 0, 1, 2, 3 or 4;

m is an integer having a value ranging from 0 to 3;

n is an integer having a value ranging from 1 to 3, as an alkylating co-catalyst in a catalytic system for polymerization based on a rare-earth metal salt.

The preferred aspects of this compound of formula (III) are identical to those of the novel compound of formula (I) defined above.

The rare-earth metal salt, according to the invention, may be represented by the formula $Ln(A)_3(B)_n$, in which Ln is the rare-earth element, A is chosen from halides, carboxylates, organophosphates, alcoholates, amides, alkyls or borohydrides and B is one or more solvent molecules complexed to the rare-earth metal and n is an integer between 0 and 3.

The expression "rare earth" is understood according to the invention to mean any element from the family of lanthanides, or yttrium or scandium. Preferably, the rare-earth element is chosen from the elements yttrium, neodymium, gadolinium or samarium, more preferably neodymium or gadolinium.

In the definition of B, the expression "complexed solvent" is understood in particular to mean ethers, amines, phosphates and thioethers. For example as an amine, mention may be made of the family of trialkylamines and aromatic amines such as pyridine or else piperazine and its derivatives. As a phosphate, mention may be made, for example, of tri-n-butyl phosphate. As a thioether, mention may be made of the family of dialkyl sulphides such as dimethyl sulphide. As an ether, mention may be made, for example of diethyl ether, 1,2-diethoxyethane, 1,2-di-n-propoxyethane, 1,2-di-n-butoxyethane, tetrahydrofuran, dioxane and tetrahydropyran. More particularly B is an ether, preferably tetrahydrofuran (THF). When A is a halide, it is preferably a chloride. B is then preferably a molecule of THF and n is equal to 2.

When A is a carboxylate, this is chosen from esters of linear or branched aliphatic carboxylic acids having 6 to 16 carbon atoms in the linear chain, and esters of substituted or unsubstituted aromatic carboxylic acids having between 6 and 12 carbon atoms. By way of example, mention may be made of the linear or branched neodecanoate (versatate), 2-ethylhexanoate or hexanoate, or else the substituted or unsubstituted naphthenate. Among the family of carboxylates, A is preferably the rare-earth 2-ethylhexanoate, naphthenate or neodecanoate.

When A is chosen from organophosphates, this includes the phosphoric acid diesters of general formula (R'O)(R"O)PO(OH), in which R' and R", which are identical or different, represent an alkyl, aryl or alkylaryl radical. Among these phosphoric acid diesters, R' and R", which are identical or different, are preferably an n-butyl, isobutyl, pentyl, amyl, isopentyl, 2,2-dimethylhexyl, 1-ethylhexyl, 2-ethylhexyl, tolyl or nonaphenoxyl radical. Among the family of organophosphates, the salt is more preferably still the rare-earth bis(2-ethylhexyl)phosphate.

When A is chosen from alcoholates, the alcoholates of an alcohol or of a polyol derived from an aliphatic or cyclic hydrocarbon and in particular from a linear or branched aliphatic hydrocarbon having 1 to 10 carbon atoms in the linear chain, more particularly 4 to 8 carbon atoms, are included. Mention may be made, for example, of neopentanolate.

When A is chosen from the family of amides, this includes, in particular, dialkylamides, N,N-bis(dialkylsilyl)amides and N,N-bis(trialkylsilyl)amides, the alkyl groups having between 1 and 10 carbon atoms.

When A is chosen from dialkylamides, B is preferably THF and n is preferably equal to 1. A is then preferably diisopropylamide and dimethylamide.

When A is chosen from N,N-bis(trialkylsilyl)amides, n is preferably equal to 0. A is then preferably the N,N-bis(trimethylsilyl)amide of formula —$N[Si(CH_3)_3]$.

When A is chosen from N,N-bis(dialkylsilyl)amides, B is preferably THF and n is preferably equal to 2 or 3. A is then preferably the N,N-bis(dimethylsilyl)amide of formula —$N[SiH(CH_3)_2]$.

When A is chosen from the family of alkyls, A is preferably a (trialkylsilyl)alkyl, such as (trimethylsilyl)methyl or bis(trimethylsilyl)methyl.

When A is chosen from the borohydrides, A is preferably tetrahydroborate, B is preferably THF and n is preferably equal to 2 or 3.

The rare-earth metal salt is preferably chosen from a rare-earth tris[di(2-ethylhexyl)phosphate], a rare-earth tri[N,N-bis(trimethylsilyl)amide] or a rare-earth tris(borohydride).

Preferably, the novel compound of formula (III) may be used in a catalytic system based on a rare-earth metal salt in proportions such that the (compound of formula (III)/rare-earth metal) molar ratio has a value ranging from 1.5 to 20 (limits included), more preferably from 2 to 12.

According to other aspects of the invention, the compound of formula (III) may be used in a catalytic system based on a rare-earth metal salt in combination with at least one component optionally present in this type of catalytic system and in particular chosen from other alkylating agents, halogen donors, and preforming conjugated dienes.

It will be noted that the organometallic compound of formula (III) combined with a rare-earth metal salt is capable of forming a catalytic system for the polymerization of conjugated dienes which makes it possible in particular to limit the steps for synthesizing a chain-end functionalized diene elastomer, while ensuring an optimal functionalization of said elastomer, that is to say with a degree of functionalization ranging from 75%, or even 90%, to 100%.

The aforementioned features of the present invention, and other features also, will be better understood on reading the following description of several exemplary embodiments of the invention, given by way of illustration and non-limitingly in relation to the appended annexes.

EXAMPLES

All of the organometallic syntheses were carried out under an inert argon atmosphere using either Schlenk techniques or a glovebox. All the solvents used during these syntheses are dried according to conventional techniques (distillation over sodium or over a molecular sieve) and are kept under an inert atmosphere. For example, the pentane and the THF are freshly distilled over sodium/benzophenone. All of the reactants come from Sigma-Aldrich, Strem and Fluka.

Syntheses

Synthesis of a Lanthanide Salt

Nd(BH$_4$)$_3$(THF)$_3$ was prepared according to a procedure described in the literature: S. Cendrowski-Guillaume, M. Nierlich, M. Lance, M. Ephritikhine, *Organometallics*, 1998, 17, 786.

Synthesis of ortho-dimethylaminobenzyl potassium [K—CH$_2$C$_6$H$_4$-o-NMe$_2$]

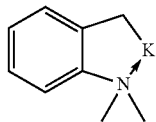

13.4 g of ortho-dimethylaminotoluine (or N,N-dimethyl-o-toluidine) (M=135 g.mol$^{-1}$; 99 mmol) are diluted in a mixture of 40 ml of hexanes and 20 ml of diethyl ether. At ambient temperature, under nitrogen and with stirring, 40 ml of a solution of butyllithium (2.5M in hexane) are added. After 3 h, 1 equivalent of $^t$BuOK is added in fractions, under argon. The solution is heated and a yellow precipitate appears. The stirring is maintained overnight. The solution is filtered and the yellow precipitate is washed three times with a mixture of hexanes (3×40 ml). After drying under vacuum, the solid is milled and dried again under vacuum overnight. 14.9 g of yellow powder of ortho-dimethylaminobenzyl potassium are obtained (yield=80%). $^1$H NMR (THF-d$^8$, 22° C.): δ=2.03 and 2.57 (2×1H, s, KCH$_2$—), 2.67 (s, 6H, —NMe$_2$), 5.11 (t, 1H, J$_{H-H}$=7 Hz, aromatic CH), 6.04 (d, 1H, J$_{H-H}$=7 Hz, aromatic CH), 6.16 (t, 1H, J$_{H-H}$=7 Hz, aromatic CH), 6.26 (t, 1H, J$_{H-H}$=7 Hz, aromatic CH).

Synthesis of bis(ortho-N,N-dimethylaminobenzyl)magnesium

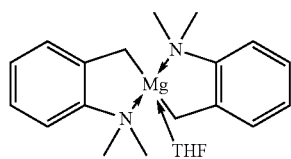

Under argon, 0.20 g of MgCl$_2$ (2.1 mmol) and 0.70 g of ortho-N,N-dimethylaminobenzyl potassium (4.0 mmol) are introduced into a Schlenk flask. Around 25 ml of THF are recondensed under vacuum at −78° C. The mixture is stirred at ambient temperature for 30 minutes, then heated at reflux under static vacuum for 5 h, at 50° C. The insoluble MgCl$_2$ crystals have then disappeared. After 1 night at 50° C., the mixture is centrifuged; the white-grey centrifugation pellet of KCl is removed, and the orange solution is concentrated to 1-2 ml, then around 0.5 ml of petroleum ether is added. Colourless crystals appear in the red solution. XRD analysis (Annex 4) of one of the crystals indicates a monomeric structure of the bis(ortho-N,N-dimethylaminobenzyl)magnesium complex (THF). M=0.30 g (yield=42%). $^1$H NMR (THF-d8, 22° C.): δ=7.00 (d, 2H, CH(6), J$_{(C-H)}$=7 Hz), 6.90 (d, 2H, CH(3), J$_{(C-H)}$=7 Hz), 6.75 (t, 2H, CH(4), J$_{(C-H)}$=7 Hz), 6.55 (t, 2H, CH(5), J$_{(C-H)}$=7 Hz), 3.65 (t, 4H, free non-deuterated THF), 2.65 (s, 12H, C(8) and C(9), N(CH$_3$)$_2$), 1.80 (m, 4H, free non-deuterated THF), 1.17 (s, 4H, C(1), Mg—CH$_2$—).
$^{13}$C NMR (THF-d8): δ=152.8 (C(2)), 148.4 (C(7)), 128.9 (C(6)), 125.9 (C(4)), 118.9 (C(5)), 118.4 (C(3)), 45.7 (N(CH$_3$)$_2$), 19.0 (Mg—CH$_2$—).

Polymerizations

Procedure

A "Steinie" bottle, previously washed and dried, and equipped with a cap and with an airtight and leaktight seal is used as a polymerization reactor. The butadiene polymerization reactions are carried out at a temperature between 50° C. and 60° C. and under an inert atmosphere (nitrogen).

For each polymerization, methylcyclohexane is introduced into said bottle as the polymerization solvent. This methylcyclohexane is sparged with nitrogen for 10 minutes to eliminate the volatile impurities.

A "polymerization solvent (methylcyclohexane)/monomer (butadiene)" weight ratio of between 5 and 7 is used (this weight ratio is referred to as S/M hereinbelow).

The neodymium-based precursor, that is to say neodymium tris(borohydride), and the functional co-catalyst are air-sensitive compounds. For this reason, they are introduced by means of glass ampoules sealed under an inert gas, which are then broken at the start of the polymerization reaction.

The amount of catalytic base made of neodymium and the amount of alkylating agent are expressed in μmol and in μMcm (μmol per 100 grams of monomer). Methanol (1 ml) or acetylacetone (used in excess) are used to stop the polymerization reactions. N-1,3-Dimethylbutyl-N'-phenyl-p-phenylenediamine (6PPD) and AO2246 are used as a protective agent for the polymer solutions obtained (at a weight of 0.2 g of each per 100 g of elastomer).

The polybutadienes are then extracted from the polymer solutions thus obtained, either by steam stripping in the presence of calcium tamolate and either drying on rolls at 100° C. or drying in an oven at 60° C. under vacuum with a slight stream of nitrogen, or by partial vacuum devolatilization with nitrogen purging at 50° C.

Control Test

Introduced successively into a Steinie bottle are 35 ml of methylcyclohexane solvent, 5.0 g of butadiene, 180 μmol of butyloctyl magnesium and one sealed glass ampoule containing 20 μmol of Nd(BH$_4$)$_3$(THF)$_3$.

The ampoule is broken under the effect of the mechanical stirring, then the reaction medium is heated to a temperature of 60° C. After 20 minutes, the polymerization reaction is stopped by addition of methanol, the polymer is coagulated, antioxidized then dried. Thus, 5.0 g of polybutadienes are obtained. The characterizations of this polymer are given in the table below.

Test 1

Introduced successively into a Steinie bottle are 35 ml of methylcyclohexane solvent, 5.2 g of butadiene and two sealed glass ampoules each containing 21 μmol of Nd(BH$_4$)$_3$(THF)$_3$ and 174 μmol of bis(ortho-N,N-dimethylaminobenzyl) magnesium.

The ampoules are broken under the effect of the mechanical stirring, then the reaction medium is heated to a temperature of 60° C. After 20 minutes, the polymerization reaction is stopped by addition of methanol, the polymer is coagulated, antioxidized then dried. Thus, 5.2 g of polybutadienes are obtained. The characterizations of this polymer are given in the table below.

Test 2

Introduced successively into a Steinie bottle are 70 ml of methylcyclohexane solvent, 7.8 g of butadiene and two sealed glass ampoules each containing 20 µmol of Nd(BH$_4$)$_3$(THF)$_3$ and 181 µmol of bis(ortho-N,N-dimethylaminobenzyl) magnesium.

The ampoules are broken under the effect of the mechanical stirring, then the reaction medium is heated to a temperature of 55° C. After 7 minutes, the polymerization reaction is stopped by addition of methanol, the polymer is coagulated, antioxidized then dried. Thus, 7.8 g of polybutadienes are obtained. The characterizations of this polymer are given in the table below.

ml/min, the temperature of the system is 35° C. and the analysis time is 90 min. Use is made of a set of four Waters columns in series, having the trade names Styragel HMW7, Styragel HMW6E and two Styragel HT6E.

The injected volume of the solution of the polymer sample is 100 µl. The detector is a Waters 2410 differential refractometer and the operating software for the chromatographic data is the Waters Empower system.

The average molecular weights calculated are relative to a calibration curve produced for polybutadienes having the following microstructure: 11 wt % of 1,2-type units and 48 wt % of trans-1,4-type units.

Table of results

| ref | Nd(BH$_4$)$_3$(THF)$_3$ µmol (µMcm) | Co-catalyst Nature[a] | Co-catalyst µmol (µMcm) | Nd/Mg ratio | S/M | Conversion (time in min.) | Average activity kg/mol[Nd]/h | $M_n$ in g/mol[b] ($I_p$) | 1,2[c] | 1,4-trans[c] | 1,4-cis[c] | % functionalized chains[d] |
|---|---|---|---|---|---|---|---|---|---|---|---|---|
| Control | 20 (400) | BOMAG | 180 | 9 | 5.4 | 100% (20) | 750 | 29 250 (1.33) | 46.1 | 29.4 | 24.5 | na[e] |
| Test 1 | 21 (404) | Mg(RN)$_2$ | 174 | 8.3 | 5.2 | 100% (20) | 780 | 27 500 (1.28) | 46.6 | 28.7 | 24.7 | 100% |
| Test 2 | 20 (256) | Mg(RN)$_2$ | 181 | 9.1 | 6.9 | 100% (7) | 3 343 | 30 000 (1.33) | 42.1 | 33.3 | 24.6 | 100% |

[a]BOMAG = butyloctyl magnesium; Mg(RN)2 = bis(ortho-N,N-dimethylaminobenzyl) magnesium
[b]$M_n$ and $I_p$ are determined by size exclusion chromatography (Annex 1)
[c]The microstructure is determined by a near infrared method (Annex 2)
[d]The proportion of chains functionalized by the dimethylaminobenzyl group is determined by $^1$H and $^{13}$C NMR (see Annex 3)
[e]na stands for "not applicable"

Annex 1

Determination of the Molecular Weight Distribution of the Polybutadienes Obtained by the Size Exclusion Chromatography (SEC) Technique a) Principle of the Measurement:

Size exclusion chromatography (SEC) makes it possible to separate the macromolecules in solution, according to their size, through columns filled with a porous gel. The macromolecules are separated according to their hydrodynamic volume, the bulkiest being eluted first.

Without being an absolute method, SEC makes it possible to comprehend the molecular weight distribution of a polymer. From commercial calibration products, the various number-average molecular weights ($M_n$) and weight-average molecular weights ($M_w$) can be determined and the polydispersity index ($I_p=M_w/M_n$) can be calculated via a Moore calibration.

b) Polymer Preparation:

There is no particular treatment of the polymer sample before analysis. It is simply dissolved in (tetrahydrofuran+1 vol % of diisopropylamine+1 vol % of triethylamine+1 vol % of distilled water) to a concentration of around 1 g/l. Then the solution is filtered over a filter with a porosity of 0.45 µm before injection.

c) SEC Analysis:

The equipment used is a Waters Alliance chromatograph. The elution solvent is (tetrahydrofuran+1 vol % of diisopropylamine+1 vol % of triethylamine), the flow rate is 0.7

Annex 2

Determination of the Microstructure of the Prepared Polymers by Near Infrared Spectroscopy (NIR)

The assaying technique known as "near infrared" (NIR) was used. This is an indirect method using "control" elastomers, the microstructure of which has been measured by the $^{13}$C NMR technique. Use is made of the quantitative relationship (Beer-Lambert law) that exists between the distribution of the monomers in an elastomer and the shape of the NIR spectrum of this elastomer. This technique is carried out in two stages:

1) Calibration:

The respective spectra of the "control" elastomers are acquired.

A mathematical model is established that associates a microstructure with a given spectrum, this using the PLS (Partial Least Squares) regression method based on a factorial analysis of the spectral data. The following two documents deal in depth with the theory and the implementation of this "multivariate" data analysis method:

(1) P. GELADI and B. R. KOWALSKI

"Partial Least Squares regression: a tutorial",

Analytica Chimica Acta, vol. 185, 1-17 (1986).

(2) M. TENENHAUS

"La régression PLS—Théorie et pratique" [PLS regression—Theory and Practice]

Paris, Editions Technip (1998).

2) Measurement:
The spectrum of the sample is recorded.
The microstructure is calculated.

Annex 3

Characterization of the Prepared Polymers by NMR.
Identification and Quantification of the Functions
Present at the Chain End The polymers are analysed by $^1$H and $^{13}$C NMR using a Bruker AV500 spectrometer equipped with a BBI $^1$H-X 5 mm probe. The solvent used for the analysis is a mixture of $CS_2$ and $C_6D_{12}$. The calibration is carried out starting from the protonated impurity of $CS_2$, with a chemical shift of 7.12 ppm.

The $^1$H and $^2$D NMR spectra confirm the presence of the dimethylaminobenzyl group at the chain end of the polybutadienes prepared. The chemical shifts of each type of proton have been attributed and information on them is given in the figure:

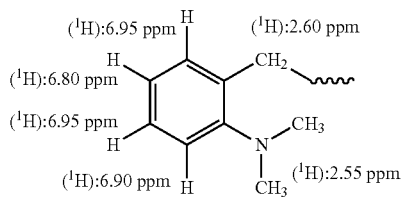

The quantification of the number of functional chains is carried out either from the signal of the aromatic proton at 6.80 ppm, which integrates for one proton, or from the broad peak between 2.7 and 2.3 ppm (—N(CH$_3$)$_2$ groups and CH$_2$ groups at the alpha position of the aromatic ring), which integrates for 8 protons. These values are related to the integration of the characteristic signals of the cis-1,4-, trans-1,4- and 1,2-units of polybutadiene. The two calculation methods result in values that are statistically identical to one another.

The invention claimed is:

1. A method of producing a catalytic system for polymerization based on a rare earth metal salt comprising introducing an organometallic compound of formula (III):

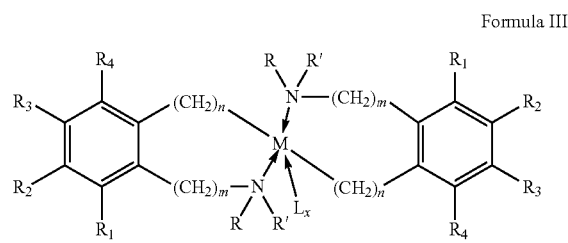

Formula III in which,

M is a metal belonging to the $2^{nd}$ column of the Periodic Table;

$R_1$, $R_2$, $R_3$ and $R_4$, which are identical to or different from one another, are hydrogen atoms or linear or branched alkyl substituents, or aryl substituents, which are substituted or unsubstituted, optionally bonded together to form at least one ring composed of 5 or 6 atoms, or at least one aromatic ring;

R and R', which are identical to or different from one another, denote linear or branched alkyl substituents, or aryl substituents, which are substituted or unsubstituted;

L is a Lewis base;

x is an integer which is equal to 0, 1, 2, 3 or 4;

m is an integer having a value ranging from 0 to 3;

n is an integer having a value ranging from 1 to 3, as an alkylating co-catalyst in the catalytic system.

2. The method according to claim 1, wherein the (compound of formula (III)/rare-earth metal) molar ratio has a value ranging from 1.5 to 20.

* * * * *